(12) United States Patent
Tomomura et al.

(10) Patent No.: US 8,207,111 B2
(45) Date of Patent: Jun. 26, 2012

(54) METHOD FOR TREATING MUSCULAR DYSTROPHY

(76) Inventors: Akito Tomomura, Sakado (JP); Mineko Tomomura, Kobe (JP); Akihiko Hirata, Kobe (JP); Takeru Fujii, Kobe (JP)

( * ) Notice: Subject to any disclaimer, the term of this patent is extended or adjusted under 35 U.S.C. 154(b) by 246 days.

(21) Appl. No.: 12/801,055

(22) Filed: May 19, 2010

(65) Prior Publication Data

US 2011/0015116 A1 Jan. 20, 2011

Related U.S. Application Data

(62) Division of application No. 11/865,462, filed on Oct. 1, 2007, now abandoned.

(60) Provisional application No. 60/929,034, filed on Jun. 8, 2007.

(30) Foreign Application Priority Data

Dec. 28, 2006 (JP) .................... 2006-355346

(51) Int. Cl.
*A61K 38/43* (2006.01)
*A61K 38/17* (2006.01)
*C12N 9/66* (2006.01)

(52) U.S. Cl. .................. 514/1.2; 514/21.2; 435/218

(58) Field of Classification Search .................. 514/1.2, 514/21.2; 435/218
See application file for complete search history.

(56) References Cited

FOREIGN PATENT DOCUMENTS

| EP | 0 768 378 | | 4/1997 |
|----|-----------|---|--------|
| EP | 768378 A1 | * | 4/1997 |
| JP | 4-279598 | | 10/1992 |
| JP | 8-298990 | | 11/1996 |
| WO | 96/00287 | | 1/1996 |
| WO | WO 9600287 A1 | * | 1/1996 |

OTHER PUBLICATIONS

Takaoka et al., "The pancreas: A storehouse of protein anabolic factors and bone/calcium metabolism-regulating factors," J Bone Miner Metab 18:2-8, 2000.*
Y. Takaoka et al., "The Pancreas: A Storehouse of Protein Anabolic Factors and Bone/Calcium Metabolism-Regulating Factors", Journal of Bone and Mineral Metabolism, vol. 18, pp. 2-8, 2000.
A. Tomomura et al., "Molecular Cloning and Expression of Serum Calcium-Decreasing Factor (Caldecrin)",The Journal of Biological Chemistry vol. 270, No. 51, pp. 30315-30321, Dec. 22, 1995.
Y. Takaoka et al., "Hypocalcemic Action of a Pancreatic Factor and its Clinical Significance on the Myasthenic Patients", Acta med. Nagasaki., vol. 13, No. 1-2, pp. 28-35, 1969.
A. Tomomura et al., "Serum Calcium-Decreasing Factor (Caldecrin) from Porcine Pancreas has Proteolytic Activity which has no Clear Connection with the Calcium Decrease", FEBS Letters, vol. 301, No. 3, pp. 277-281, Apr. 1992.
Y. Takaoka et al., "Relation of the Parotid Gland to Serum Protein and Malnutrition", The Tohoku Journal of Experimental Medicine, vol. 57, No. 1, pp. 9-15, 1952.
Y. Takaoka et al., "Hypertrophy of Parotid Glands in Diabetes Mellitus and Internal Secretion of Salivary Glands", The Japanese Medical Journal, vol. 3, No. 3, pp. 199-203, Jun. 1950.

(Continued)

*Primary Examiner* — Rosanne Kosson
(74) *Attorney, Agent, or Firm* — Wenderoth, Lind & Ponack, L.L.P.

(57) ABSTRACT

The object of the present invention is to provide a method for treating muscular dystrophy. The method for treating muscular dystrophy according to the present invention is characterized in comprising a step of administering a caldecrin.

6 Claims, 3 Drawing Sheets

OTHER PUBLICATIONS

Y. Takaoka et al., "A Pancreatic Protein Anabolic Extract", Acta med. Nagasaki, vol. 10, pp. 51-57, 1965.

Y. Takaoka et al., "The Vision of Therapeutic Agent for Progressive Muscle Dystrophy", Saishin Igaku (the most recent medical science), vol. 35, No. 5, pp. 999-1007, 1980, with partial English translation, 1st page only.

Y. Takaoka et al., "Proposal of New Protein Anabolic Hormone Derived from Pancreas", Nihon Iji Shinpou (Courier of Japanese Medical Business), No. 2951, pp. 15-20, Nov. 15, 1980, with a partial English translation, 1st page only.

Restriction Requirement issued on Feb. 4, 2009 in parent U.S. Appl. No. 11/865,462.

Restriction Requirement issued on May 7, 2009 in U.S. Appl. No. 11/865,462.

Office Action issued on Feb. 19, 2010 in U.S. Appl. No. 11/865,462.

I. Yoshino-Yasuda et al., "Caldecrin is a Novel-Type Serine Protease Expressed in Pancreas, but its Homologue, Elastase IV, is an Artifact During Cloning Derived from Caldecrin Gene", J. Biochem., vol. 123, pp. 546-554, 1998.

Result 2, Alignment of Instant SEQ ID No. 2 with the Polypeptide of Tomomura et al. (WO 96/00287A1 or EP 768378A1) from a search in Geneseq database performed on Dec. 18, 2009.

BLAST Sequence Comparison of SEQ ID Nos. 1 and 2, performed on NCBI BLAST Website on Apr. 21, 2009 and cited in Restriction Requirement issued May 7, 2009 in parent application.

* cited by examiner

SEQUENCE LISTING

```
<160> NUMBER OF SEQ ID NOS: 12

<210> SEQ ID NO 1
<211> LENGTH: 252
<212> TYPE: PRT
<213> ORGANISM: Rat

<400> SEQUENCE: 1

Cys Gly Asn Pro Ala Phe Pro Pro Asn Leu Ser Thr Arg Val Val Gly
1               5                   10                  15

Gly Glu Asp Ala Val Pro Asn Ser Trp Pro Trp Gln Val Ser Leu Gln
            20                  25                  30

Tyr Leu Lys Asp Asp Thr Trp Arg His Thr Cys Gly Gly Ser Leu Ile
        35                  40                  45

Thr Thr Ser His Val Leu Thr Ala Ala His Cys Ile Asn Lys Asp Phe
    50                  55                  60

Thr Tyr Arg Val Gly Leu Gly Lys Tyr Asn Leu Thr Val Glu Asp Glu
65                  70                  75                  80

Glu Gly Ser Val Tyr Ala Glu Val Asp Thr Ile Tyr Val His Glu Lys
                85                  90                  95

Trp Asn Arg Leu Phe Leu Trp Asn Asp Ile Ala Ile Lys Leu Ala
            100                 105                 110

Glu Pro Val Glu Leu Ser Asn Thr Ile Gln Val Ala Cys Ile Pro Glu
        115                 120                 125

Glu Gly Ser Leu Leu Pro Gln Asp Tyr Pro Cys Tyr Val Thr Gly Trp
    130                 135                 140

Gly Arg Leu Trp Thr Asn Gly Pro Ile Ala Glu Val Leu Gln Gln Gly
145                 150                 155                 160

Leu Gln Pro Ile Val Ser His Ala Thr Cys Ser Arg Leu Asp Trp Trp
```

```
                    165                 170                 175
Phe Ile Lys Val Arg Lys Thr Met Val Cys Ala Gly Gly Asp Gly Val
                180                 185                 190

Ile Ser Ala Cys Asn Gly Asp Ser Gly Gly Pro Leu Asn Cys Gln Ala
            195                 200                 205

Glu Asp Gly Ser Trp Gln Val His Gly Ile Val Ser Phe Gly Ser Ser
        210                 215                 220

Ser Gly Cys Asn Val His Lys Lys Pro Val Val Phe Thr Arg Val Ser
225                 230                 235                 240

Ala Tyr Asn Asp Trp Ile Asn Glu Lys Ile Gln Leu
                245                 250

<210> SEQ ID NO 2
<211> LENGTH: 252
<212> TYPE: PRT
<213> ORGANISM: Homo sapiens
<220> FEATURE:
<221> NAME/KEY: misc_feature
<222> LOCATION: (64)..(64)
<223> OTHER INFORMATION: Xaa can be any naturally occurring amino acid

<400> SEQUENCE: 2

Cys Gly Val Pro Ser Phe Pro Pro Asn Leu Ser Ala Arg Val Val Gly
1               5                   10                  15

Gly Glu Asp Ala Arg Pro His Ser Trp Pro Trp Gln Ile Ser Leu Gln
            20                  25                  30

Tyr Leu Lys Asn Asp Thr Trp Arg His Thr Cys Gly Gly Thr Leu Ile
        35                  40                  45

Ala Ser Asn Phe Val Leu Thr Ala Ala His Cys Ile Ser Asn Thr Xaa
    50                  55                  60

Thr Tyr Arg Val Ala Val Gly Lys Asn Asn Leu Glu Val Glu Asp Glu
65                  70                  75                  80

Glu Gly Ser Leu Phe Val Gly Val Asp Thr Ile His Val His Lys Arg
                85                  90                  95

Trp Asn Ala Leu Leu Leu Arg Asn Asp Ile Ala Leu Ile Lys Leu Ala
            100                 105                 110

Glu His Val Glu Leu Ser Asp Thr Ile Gln Val Ala Cys Leu Pro Glu
        115                 120                 125

Lys Asp Ser Leu Leu Pro Lys Asp Tyr Pro Cys Tyr Val Thr Gly Trp
    130                 135                 140

Gly Arg Leu Trp Thr Asn Gly Pro Ile Ala Asp Lys Leu Gln Gln Gly
145                 150                 155                 160

Leu Gln Pro Val Val Asp His Ala Thr Cys Ser Arg Ile Asp Trp Trp
                165                 170                 175

Gly Phe Arg Val Lys Lys Thr Met Val Cys Ala Gly Gly Asp Gly Val
            180                 185                 190

Ile Ser Ala Cys Asn Gly Asp Ser Gly Gly Pro Leu Asn Cys Gln Leu
        195                 200                 205

Glu Asn Gly Ser Trp Glu Val Phe Gly Ile Val Ser Phe Gly Ser Arg
    210                 215                 220

Arg Gly Cys Asn Thr Arg Lys Lys Pro Val Val Tyr Thr Arg Val Ser
225                 230                 235                 240

Ala Tyr Ile Asp Trp Ile Asn Glu Lys Met Gln Leu
                245                 250

<210> SEQ ID NO 3
<211> LENGTH: 756
```

```
<212> TYPE: DNA
<213> ORGANISM: Rat

<400> SEQUENCE: 3
tgcgggaacc ccgccttccc acctaacctg tcaaccagag tggtaggagg agaggatgct      60
gtccccaaca gctggccttg gcaggtctct ctccagtacc tcaaggacga cacatggagg     120
cacacctgtg ggggaagtct catcaccacc agccacgtcc tcactgccgc ccactgcatc     180
aacaaagact tcacttaccg tgtgggcctg ggaagtata atctgacagt ggaggatgag      240
gaaggctccg tgtacgctga ggtggacacc atctacgtcc atgagaagtg gaaccgactc     300
ttcctgtgga acgacatcgc tatcattaag ttggctgagc ctgtggaact gagcaacacc     360
atccaggtgg cctgcatccc agaggaaggt tccctgctgc tcaggacta tccctgctat      420
gtcacgggct ggggtcgcct ctggaccaat ggtcccatcg ctgaagtgct ccagcagggc     480
ctgcagccca tcgtgagcca tgccacgtgc tccaggttgg actggtggtt catcaaggtc     540
cggaagacga tggtgtgcgc tgggggtgat ggcgtcatct ctgcctgtaa cggagattct     600
ggcggcccac tgaactgcca agcagaagac ggctcatggc aggtgcacgg catcgtgagc     660
ttcggttcca gtagcggctg caacgtacac aagaaaccgg tagtcttcac ccgagtgtct     720
gcctacaatg actggatcaa cgagaaaata caactg                              756

<210> SEQ ID NO 4
<211> LENGTH: 756
<212> TYPE: DNA
<213> ORGANISM: Homo sapiens
<220> FEATURE:
<221> NAME/KEY: misc_feature
<222> LOCATION: (190)..(190)
<223> OTHER INFORMATION: n is a, c, g, or t

<400> SEQUENCE: 4
tgtggggtgc ccagcttccc gcccaaccta tccgcccgag tggtgggagg agaggatgcc      60
cggcccccaca gctggccctg gcagatctcc ctccagtacc tcaagaacga cacgtggagg     120
catacgtgtg gcgggacttt gattgctagc aacttcgtcc tcactgccgc ccactgcatc     180
agcaacaccn ggacctaccg tgtggccgtg ggaaagaaca acctggaggt ggaagacgaa     240
gaaggatccc tgtttgtggg tgtggacacc atccacgtcc acaagagatg gaatgccctc     300
ctgttgcgca atgatattgc cctcatcaag cttgcagagc atgtggagct gagtgacacc     360
atccaggtgg cctgcctgcc agagaaggac tccctgctcc ccaaggacta cccctgctat     420
gtcaccggct ggggccgcct ctggaccaac ggccccattg ctgataagct gcagcagggc     480
ctgcagcccg tggtggatca cgccacgtgc tccaggattg actggtgggg cttcagggtg     540
aagaaaacca tggtgtgcgc tggggggcgat ggcgtcatct cagcctgcaa tgggactcc      600
ggtggcccac tgaactgcca gttggagaac ggttcctggg aggtgtttgg catcgtcagc     660
tttggctccc ggcggggctg caacacccgc aagaagccgg tagtctacac ccgggtgtcc     720
gcctacatcg actggatcaa cgagaaaatg cagctg                              756

<210> SEQ ID NO 5
<211> LENGTH: 756
<212> TYPE: DNA
<213> ORGANISM: Rat

<400> SEQUENCE: 5
tgcgggaacc ccgccttccc acctaacctg tcaaccagag tggtaggagg agaggatgct      60
gtccccaaca gctgggcttg gcaggtctct ctccagtacc tcaaggacga cacatggagg     120
```

```
cacacctgtg ggggaagtct catcaccacc agccacgtcc tcactgccgc ccactgcatc    180
aacaaagact tcacttaccg tgtgggcctg gggaagtata atctgacagt ggaggatgcg    240
gaggctccgt gtacactgag gtggacacca tctacgtcca tgagaagtgg aaccgactct    300
tcctgtggaa ccgacatcgc tatcattaag ttggctgagc ctgtggaact gagcaacacc    360
atccaggtgg cctgcatccc agaggaaggt tccctgctgc ctcaggacta tccctgctat    420
gtcacgggct ggggtcgcct ctggaccaat ggtcccatcg ctgaagtgct ccagcagggc    480
ctgcagccca tcgtgagcca tgccacgtgc tccaggttgg actggtggtt catcaaggtc    540
cggaagacga tggtgtgcgc tgggggtgat ggcgtcatct ctgcctgtaa cggagattct    600
ggcggcccac tgaactgcca agcagaagac ggctcatggc aggtgcacgg catcgtgagc    660
ttcggttcca gtagcggctg caacgtacac aagaaaccgg tagtcttcac ccgagtgtct    720
gcctacaatg actggatcaa cgagaaaata caactg                              756
```

<210> SEQ ID NO 6
<211> LENGTH: 252
<212> TYPE: PRT
<213> ORGANISM: Rat

<400> SEQUENCE: 6

```
Cys Gly Asn Pro Ala Phe Pro Pro Asn Leu Ser Thr Arg Val Val Gly
  1               5                  10                  15

Gly Glu Asp Ala Val Pro Asn Ser Trp Ala Trp Gln Val Ser Leu Gln
                 20                  25                  30

Tyr Leu Lys Asp Asp Thr Trp Arg His Thr Cys Gly Gly Ser Leu Ile
             35                  40                  45

Thr Thr Ser His Val Leu Thr Ala Ala His Cys Ile Asn Lys Asp Phe
         50                  55                  60

Thr Tyr Arg Val Gly Leu Gly Lys Tyr Asn Leu Thr Val Glu Asp Ala
 65                  70                  75                  80

Glu Ala Pro Cys Thr Leu Arg Trp Thr Pro Ser Thr Met Arg Ser
                 85                  90                  95

Gly Thr Asp Ser Ser Cys Gly Thr Asp Ile Ala Ile Lys Leu Ala
            100                 105                 110

Glu Pro Val Glu Leu Ser Asn Thr Ile Gln Val Ala Cys Ile Pro Glu
            115                 120                 125

Glu Gly Ser Leu Leu Pro Gln Asp Tyr Pro Cys Tyr Val Thr Gly Trp
        130                 135                 140

Gly Arg Leu Trp Thr Asn Gly Pro Ile Ala Glu Val Leu Gln Gln Gly
145                 150                 155                 160

Leu Gln Pro Ile Val Ser His Ala Thr Cys Ser Arg Leu Asp Trp Trp
                165                 170                 175

Phe Ile Lys Val Arg Lys Thr Met Val Cys Ala Gly Gly Asp Gly Val
            180                 185                 190

Ile Ser Ala Cys Asn Gly Asp Ser Gly Gly Pro Leu Asn Cys Gln Ala
        195                 200                 205

Glu Asp Gly Ser Trp Gln Val His Gly Ile Val Ser Phe Gly Ser Ser
    210                 215                 220

Ser Gly Cys Asn Val His Lys Lys Pro Val Val Phe Thr Arg Val Ser
225                 230                 235                 240

Ala Tyr Asn Asp Trp Ile Asn Glu Lys Ile Gln Leu
                245                 250
```

```
<210> SEQ ID NO 7
<211> LENGTH: 16
<212> TYPE: PRT
<213> ORGANISM: Rat

<400> SEQUENCE: 7

Met Leu Gly Ile Thr Val Leu Ala Ala Ile Leu Ala Cys Ala Ser Cys
1               5                   10                  15

<210> SEQ ID NO 8
<211> LENGTH: 16
<212> TYPE: PRT
<213> ORGANISM: Homo sapiens

<400> SEQUENCE: 8

Met Leu Gly Ile Thr Val Leu Ala Ala Leu Leu Ala Cys Ala Ser Ser
1               5                   10                  15

<210> SEQ ID NO 9
<211> LENGTH: 35
<212> TYPE: DNA
<213> ORGANISM: Artificial Sequence
<220> FEATURE:
<223> OTHER INFORMATION: Synthetic construct

<400> SEQUENCE: 9
catggtctct aatgttgggc atcactgtcc tcgct                              35

<210> SEQ ID NO 10
<211> LENGTH: 35
<212> TYPE: DNA
<213> ORGANISM: Artificial Sequence
<220> FEATURE:
<223> OTHER INFORMATION: Synthetic construct

<400> SEQUENCE: 10
catggtctca gcgctcagct gcattttctc gttga                              35

<210> SEQ ID NO 11
<211> LENGTH: 35
<212> TYPE: DNA
<213> ORGANISM: Artificial Sequence
<220> FEATURE:
<223> OTHER INFORMATION: Synthetic construct

<400> SEQUENCE: 11
atgttgggca tcactgtcct cgctgcgctc ttggc                              35

<210> SEQ ID NO 12
<211> LENGTH: 35
<212> TYPE: DNA
<213> ORGANISM: Artificial Sequence
<220> FEATURE:
<223> OTHER INFORMATION: Synthetic construct

<400> SEQUENCE: 12
ctagcggccg ctcacagctg cattttctcg ttgat                              35
```

METHOD FOR TREATING MUSCULAR DYSTROPHY

This application claims the benefit of priority to Japanese patent application No. 2006-355346 filed on Dec. 28, 2006, and provisional patent application in the U.S. No. 60/929,034 filed on Jun. 8, 2007, the contents of which are incorporated by reference herein. In addition, this application is a divisional application of U.S. application Ser. No. 11/865,462, filed on Oct. 1, 2007, now abandoned, the contents of which are incorporated herein by reference.

BACKGROUND OF THE INVENTION

1. Field of the Invention

The present invention relates to a method for treating muscular dystrophy.

2. Description of the Related Art

Main pathological changes by muscular dystrophy are degeneration and necrosis of skeletal muscle. Clinically, muscular dystrophy is a genetic disease accompanied with progressive loss of muscle strength.

As causes of muscular atrophy leading to a loss of muscle strength, an abnormality of in motor nerves in addition to an abnormality of muscle itself is exemplified. A muscular atrophy due to an abnormality of muscle itself is called as myogenic muscular atrophy, and a muscular atrophy due to an abnormality of motor nerves is called as neurogenic muscular atrophy. In neurogenic muscular atrophy, no abnormality is found in muscle but an abnormality appears in motor nerves and muscles movement, leading to muscular atrophy. Muscular dystrophy is a representative disease of myogenic muscular atrophy.

Although the cause of muscular dystrophy is not quite clear, deficiencies and abnormalities in a series of proteins of dystrophin present just below a muscular plasma membrane, adhalin present in a plasma membrane, merosin present in a basement membrane and the like are considered as possible causes.

Based on such knowledge, it is considered as a possible treatment for muscular dystrophy to induce dystrophin and the like. However, their effectiveness has not been confirmed in clinical trials.

As a therapeutic drug, a protein anabolic hormone, a growth hormone, a calcium antagonist, a protein-degrading enzyme inhibitor such as bestatin, a muscle relaxant such as sodium dantrolene and the like have been used so far. However, although these drugs exhibit a certain degree of inhibiting effect on progression of symptoms at an initial period of administration, the effect does not last. Thus, in the present situation, rehabilitation and the like are mainly carried out as a treatment for preventing progression of dysfunction. Namely, the drugs having a sufficient therapeutic effect on muscular dystrophy have not been known. Therefore, drugs for treating muscular dystrophy have been studied.

For example, it is described in TAKAOKA et al., Journal of Bone and Mineral Metabolism, vol. 18, pp. 2-8 (2000), that a patient of progressive muscular dystrophy who had almost been immobilized for 4 years was administered a crude extract derived from pig pancreas. As a result, an improvement was seen in one week, and the patient could go back home in one month. It is further described in the document that a muscular dystrophy patient was administered the same crude extract, so that the patient gained weight in 8 months and came to be able to raise the leg high in 10 months.

However, precise experimental conditions are not described in the above academic document at all, so the reliability of the results is questionable. For example, it is unlikely that no other treatment was taken at all while the crude extract was administered; therefore, there is no certain evidence that the above improvement effects are resulted from the crude extract alone. In fact, although it is described in the document that the above crude extract has a strong activity for reducing BUN, i.e. serum urea nitrogen level, which is to be an indicator of muscular dystrophy, the effect was weak when the present inventors carried out a similar experiment.

In the above academic document, it is also described that N-terminal amino acid sequence of the protein further purified from the crude extract indicates high homology with human elastase IIIB. In addition, it is concluded that bone/calcium metabolism regulating activity of the crude extract results from elastase IIIB.

However, the effects of human elastase IIIB on muscular dystrophy have not been proved directly, and there is no report of its clinical use. Of course, it has not been put to practical use.

Tomomura who is one of the inventors of the present invention isolated caldecrin from pig pancreas and found that the caldecrin reduces serum calcium level (Japanese unexamined patent publication No. 4-279598). Further, Tomomura completed method of producing caldecrin using a caldecrin gene (Japanese unexamined patent publication No. 8-298990). However, the effects of the caldecrin on muscular dystrophy have never reported so far.

BRIEF SUMMARY OF THE INVENTION

As described above, muscular dystrophy is an intractable disease accompanied with a gradual loss of motor function, and its fundamental treatment method has not been established. Further, various studies have been carried out with respect to muscular dystrophy, but there is no drug that has been put to practical use and exerts sufficient effect.

PX, which is a crude extract derived from pig pancreas, is reported in the above academic document to have indicated marked effects on muscular dystrophy, but has not been put to practical use. Though the reason is unknown, according to the experiment by the present inventors, PX does not have a markedly superior effect on reduction of BUN and PX has a defect of increasing creatinine level in blood. Creatinine is normally excreted directly into urine, but if there is an abnormality in renal function, it is accumulated in blood. Thus, creatinine is used as an evaluation index of renal functions. Namely, PX has a problem of lowering renal functions.

The problem to be solved by the present invention is to provide a method for treating muscular dystrophy, using a drug which has a therapeutic effect on muscular dystrophy and does not lower renal functions.

The present inventors intensively studied for solving the above problem, and accomplished the present invention with a finding that caldecrin and a caldecrin gene show an excellent therapeutic effect on muscular dystrophy without damaging renal functions.

A first method for treating muscular dystrophy according to the present invention is characterized in comprising a step of administering a caldecrin.

A second method for treating muscular dystrophy according to the present invention is characterized in comprising a step of a following protein selected from (a) to (d):

(a) a protein having amino acid sequence of SEQ ID NO: 1;
(b) a protein having amino acid sequence of SEQ ID NO: 2;

(c) a protein formed by deletion, substitution and/or addition of 1 to 10 amino acids of a protein having the amino acid sequence of SEQ ID NO: 1, and having therapeutic effect on muscular dystrophy;
(d) a protein formed by deletion, substitution and/or addition of 1 to 10 amino acids of a protein having the amino acid sequence of SEQ ID NO: 2, and having therapeutic effect on muscular dystrophy.

DETAILED DESCRIPTION OF THE INVENTION

The therapeutic drug for muscular dystrophy according to the present invention is characterized in comprising a caldecrin.

The caldecrin is discovered by Tomomura et al. The pro-type of the caldecrin consists of 252 amino acids having a molecular weight of about 28 kDa, and the prepro-type thereof consists of 268 amino acids having a molecular weight of about 30 kDa. In mouse, the caldecrin dose-dependently lowers serum calcium concentration, and has an inhibitory activity against parathyroid hormone (PTH)-induced calcium release in embryonic bone cell culture system.

A type of the caldecrin used in the present invention is not particularly limited as long as it has a therapeutic effect on muscular dystrophy, and includes, for example, a caldecrin derived from human and a caldecrin derived from rat. Therapeutic effects of these caldecrins on muscular dystrophy are demonstrated in the following Examples.

In the caldecrin of the present invention, a mature-type, a pro-type and a prepro-type thereof are included. Besides, a caldecrin bonded to a label sequence or a marker group can also exert the same activity as the caldecrin.

The caldecrin is homologous with serine protease such as elastase and chymotrypsin. For example, a gene coding pro-type rat caldecrin (SEQ ID No.3) and a gene coding pro-type rat elastase IV (SEQ ID No.5) show high homology. However, in comparison of both sequences, adenine is inserted at 243rd in pro-type rat caldecrin gene. The insertion causes frame shift mutation. In addition, cytosine is inserted at 312th in pro-type rat elastase IV gene. As a result, in comparison between pro-type rat caldecrin (SEQ ID No.1) and pro-type rat elastase IV (SEQ ID No.6), amino acid sequences of both of the proteins are clearly different at around a middle thereof (refer to SEQ ID No. 1 and SEQ ID No. 6). Specifically, while amino acid sequences of 1st to 80th and 105th or later in pro-type rat caldecrin (SEQ ID No.1) and pro-type rat elastase IV (SEQ ID No.6) are almost same, amino acid sequences of 81st to 104th in both of the amino acid sequences are different at all by the above-mentioned insertion of adenine and cytosine, although the 81st amino acid in both of the amino acid sequences happens to be identified each other as glutamic acid in spite of the frame shift mutation.

Further, the caldecrin has a common feature with elastase IIIB, which is said to be an active component of the crude extract derived from pig pancreas, in that they have an effect of lowering serum calcium in normal mouse, but they are clearly different in their structures and the other effects.

For example, the caldecrin does not lose an effect on lowering serum calcium in mouse and an inhibitory effect on PTH, even when treated with phenyl methane sulfonyl fluoride (PMSF) which is an irreversible serine protease inhibitor. On the other hand, elastase IIIB loses an effect of lowering serum calcium and an inhibitory effect on PTH by PMSF.

Examples of the caldecrin used in the present invention may comprise the following protein selected from (a) to (d):
(a) a protein having amino acid sequence of SEQ ID NO: 1;
(b) a protein having amino acid sequence of SEQ ID NO: 2;
(c) a protein formed by deletion, substitution and/or addition of 1 to 10 amino acids of a protein having the amino acid sequence of SEQ ID NO: 1, and having therapeutic effect on muscular dystrophy;
(d) a protein formed by deletion, substitution and/or addition of 1 to 10 amino acids of a protein having the amino acid sequence of SEQ ID NO: 2, and having therapeutic effect on muscular dystrophy.

The caldecrins of SEQ ID No.1 and SEQ ID No.2 are pro-type containing pro-sequence consisting of 1st to 13th amino acids. Such a pro-type caldecrin becomes a mature-type caldecrin by breakage of the pro-sequence by, for example, protease present in living body after administration. However, the 1st cysteine forms intramolecular disulfide bond with inside cysteine, and the pro-sequence is also bound in the mature-type. Accordingly, such a mature-type is included in the proteins (c) or (d), which is formed by bonding and breakage of the pro-sequence in the proteins (a) or (b).

The proteins (c) or (d) of the present invention includes a prepro-type caldecrin in which a pre-sequence is bound at N-terminal of the proteins (a) or (b). The caldecrin is excreted as pro-type to the outside of a cell, after production inside of the cell as prepro-type and breakage of the pre-sequence. A pre-sequence of rat caldecrin is SEQ ID No.7, and a pre-sequence of human caldecrin is SEQ ID No.8.

The caldecrin according to the present invention comprises a protein formed by deletion, substitution and/or addition of one or several amino acids of a protein having amino acid sequence of SEQ ID No.1 or SEQ ID No.2, and having therapeutic effect on muscular dystrophy. For example, in order to enhance activity, stability or the like, the proteins (c) or (d) may be formed by adding an amino acid or a peptide to N-terminal or C-terminal of the proteins (a) or (b). Preferably, such an amino acid or a peptide is added to N-terminal thereof.

The number of amino acids to be deleted, substituted or added is preferably from 1 to 10, more preferably from 1 to 5, even more preferably 1 to 2. The amino acid sequence of SEQ ID No.1 or SEQ ID No.2 that has been deleted, substituted or added preferably has an identity of 80% or more with the amino acid sequence of the human caldecrin or the rat caldecrin, more preferably has an identity of 90% or more, and even more preferably an identity of 95% or more. The identity can be determined by a publicly known method using a software program such as BLAST (Basic Local Alignment Search Tool). The substituting amino acids preferably belong to the same classification of the amino acid to be substituted. Examples of such a classification include, in addition to classification such as neutral amino acid, acidic amino acid and basic amino acid, classification such as aliphatic amino acid, imino acid, and aromatic amino acid, and further, classification such as branched amino acid, hydroxy amino acid, sulfur-containing amino acid, and acid amide amino acid.

The term, "having a therapeutic effect on muscular dystrophy", in the definition in the above proteins (c) or (d) means that at least one of the effects as a therapeutic agent for muscular dystrophy is equivalent or superior to that of a protein having an amino acid sequence of SEQ ID No.1 or SEQ ID No.2. The effects of the therapeutic agent for muscular dystrophy include, in addition to alleviation of symptoms of muscular dystrophy in clinical trials and animal experiments, lowering of serum urea nitrogen which is to be an indicator of modification and necrosis of muscle fiber, and lowering of concentration of creatinine in blood which is a non-protein nitrogen compound produced from creatine in muscle and an indicator of side effects of muscular dystrophy, and the like.

A method for producing the caldecrin is not particularly limited, and the caldecrin can be produced by a publicly known method or by an improvement method based on the publicly known method.

For example, the caldecrin can be isolated and purified from rat pancreas as a natural protein according to a method by Tomomura et. al. (refer to Tomomura et al., Journal of Biological Chemistry, 270, pp. 30315-30321 (1995). The content of the document is incorporated by reference herein). In such a case, caldecrin is purified as the mature-type activated by a protease existing together.

More specifically, an acetone powder is obtained by crushing a rat pancreas followed by dehydration with acetone. From the powder, a protein is purified by repeating precipitation using acetone or ammonium sulfate, dialysis and the like, finally column chromatography. Then, a fraction containing the caldecrin alone is identified by examining lowering effect of serum calcium or amino acid sequence analysis, and the fraction is lyophilized. As a specific method for purifying the protein, there can be listed ion exchange chromatography, gel filtration chromatography, electrophoresis, affinity chromatography, reverse phase chromatography, salting out, and precipitation using acetone or ammonium sulfate, and these may be suitably used in combination.

Naturally-derived caldecrin may be derived from mammal, avian species, amphibians, reptiles, or fish, but since the caldecrin in the present invention is used for treating human muscular dystrophy, natural caldecrin is preferably derived from human.

The caldecrin can be produced as a recombinant protein by a method described in Japanese unexamined patent publication No. 4-279598, the contents of which are incorporated by reference herein, or an improvement method based on the method.

Specifically, a gene coding the prepro-type caldecrin or the like is incorporated into an appropriate vector such as IRES-GFP vector in accordance with a conventional method. Further, the vector is transfected to an appropriate cell, and the cell is cultured. Examples of the cell to be used in this case include a bacteria (prokaryotic cell) such as *Escherichia coli* and *Bacillus subtilis*; an yeast such as baker's yeast; an insect cell such as a cell derived from an ovary of a common cutworm moth (Sf9 cell line); a cell derived from an ovary of a Chinese hamster (CHO cell); a cell derived from kidney of an African green monkey (COS cell); and a mammal cell such as a kidney cell of a human fetus (HEK 293 cell). Culture conditions such as cultivation temperature and type of medium may be those suited for the cell which is to be used. After the culture, the protein is isolated and purified from the medium, the fraction containing the caldecrin alone is identified, and the fraction is subjected to lyophilizations. In such a case, caldecrin is generally obtained as pro-type.

The caldecrin used in the present invention may also be obtained by chemical synthesis in accordance with a known synthesis method of peptide.

Alternatively, the same amino acid sequence as that of a natural caldecrin derived from human or rat may be formed by deleting and/or substituting 1, 2 or more amino acids in the natural caldecrin derived from mammal other than human or rat, or adding 1, 2 or more amino acids thereto.

The caldecrin can be administered as the pro-type or the mature-type thereof. In case of that the pro-type caldecrin is administered, the pro-type caldecrin is activated in the living body into the mature-type to exert the activity. Alternatively, the pro-type caldecrin may be activated by a protease such as trypsin, and then the obtained the mature-type may be administered.

The caldecrin of the present invention can alleviate muscular dystrophy by being administered at a region of muscular atrophy or a region of loss of muscle strength. As a form of drug, injection is preferred since caldecrin is a protein. However, needle-free administration is desirable for patients, and any form of drug such as oral preparation and external preparation may be possible due to progress of technology, and thus there is no limitation in terms of the form of drug.

The above drugs of various forms can be produced by a conventional method, and common additives may be used for preparation of various forms of drugs as components other than caldecrin which is an active ingredient. For example, a lyophilization powder drug for injection is prepared by dissolving an effective dose of purified caldecrin in a diluent such as distilled water, physiological saline and a glucose aqueous solution; and adding a excipient such as carboxy methylcellulose and sodium alginate; a preservative such as benzyl alcohol, benzalkonium chloride, and phenol; a analgesia agent such as glucose, calcium gluconate, and procaine hydrochloride; a pH adjuster such as hydrochloric acid, acetic acid, citric acid, and sodium hydroxide as necessary; and lyophilizing in accordance with a conventional method.

A dose of the caldecrin which is the therapeutic drug for muscular dystrophy according to the present invention may be suitably adjusted according to symptoms, severity, age and sex of a muscular dystrophy patient, and normally the dose may be approximately in a range from 0.1 to 1 mg per kg of the body weight.

An administration of the caldecrin according to the present invention is to be carried out normally as a subcutaneous, intramuscular or intravenous injection in a single or multiple doses in a required amount, and an administration by a direct injection into the muscle may preferably enhance the effect. As an administration method, an ampule for injection can be directly injected subcutaneously, into the muscle or intravenously. In a case of intravenous injection, it is also possible to use an infusion pump for administration. Further, the therapeutic drug for muscular dystrophy of the present invention may be administered by mixing a given amount thereof in advance with a sugar infusion such as a dextrose solution in a treatment for muscular dystrophy, or an effective dose of the drug may be given as sole administration into peripheral veins and the like at the same time of the administration of sugar infusion.

In a case of a lyophilization powder drug for injection, the powder drug is diluted in distilled water, physiological saline, Ringer solution and the like before use, and is administered in the same manner as an ampule.

Another therapeutic drug for muscular dystrophy according to the present invention comprises a caldecrin gene. The therapeutic drug for muscular dystrophy is capable of alleviating symptoms of muscular dystrophy by transforming cells of atrophic muscles and muscles with lowered strength or around a diseased area so as to be able to secrete caldecrin or a protein such as caldecrin precursor containing caldecrin.

Examples of the caldecrin gene include a caldecrin gene containing a gene (SEQ ID No.3) which codes pro-type rat caldecrin and a gene (SEQ ID No.4) which codes pro-type human caldecrin. The term, "containing" a base sequence of SEQ ID No.3 or SEQ ID No.4, means that, for example, a sequence which facilitates transformation of the cells and promotes expression of caldecrin genes may be bonded before and after the base sequence. Generally, the gene coding prepro-type caldecrin is transfected. In such a case, caldecrin is biosynthesized in cell, and is excreted in the blood as pro-type.

The caldecrin gene can be produced by a conventional method in a general genetic engineering field. For example, cDNA library is first prepared from a cell which produces caldecrin using a conventional method such as reverse transcription of mRNA. From the cDNA library, cDNA containing a caldecrin gene is obtained using a probe or an antibody for identifying a caldecrin gene. The cDNA is then amplified by polymerase chain reaction and further purified by a column and the like. Then, the obtained DNA may be introduced to a cell for further increasing the amount of DNA.

The caldecrin gene is preferably introduced into a vector in order to transfer the gene to a diseased area or around the diseased area as a therapeutic drug. The vector is not particularly limited as long as it is generally used for administration to human, and for example, a plasmid vector such as pCAGGS, pIRES-GFP and pIRES-bleo may be used. The vector may be encapsulated in liposome and the like in order to facilitate incorporation of the caldecrin gene into a targeted cell by endocytosis. Additionally, a virus vector such as adenovirus may be used.

The therapeutic drug for muscular dystrophy of the present invention comprises the caldecrin or the expression vector in which the gene coding the caldecrin is inserted as active ingredients, and is preferably used together with another appropriate diluent and an additive in an appropriate form of drug.

The administration method of the therapeutic drug for muscular dystrophy containing the caldecrin gene according to the present invention is not particularly limited. For example, the therapeutic drug may be administered as an injection after being suspended in a diluent such as physiological saline followed by further adding another additive as necessary to be formed into an appropriate form of drug.

The dose of the therapeutic drug for muscular dystrophy containing the caldecrin gene according to the present invention may be also suitably adjusted according to symptoms, severity, age and sex of a muscular dystrophy patient, and normally the dose may be approximately in a range from 0.1 to 10 mg per kg of the body weight.

The cells transformed by the caldecrin gene according to the present invention secrete the caldecrin to alleviate symptoms of muscular dystrophy. Therefore, cells of a patient are transformed in vitro by the caldecrin gene of the present invention, then the transformed cells may be transplanted in the diseased area or around the diseased area to treat muscular dystrophy.

The therapeutic drug for muscular dystrophy of the present invention has a highly excellent effect on muscular dystrophy. Further, the therapeutic drug does not impart any damage to renal function. Therefore, the therapeutic drug for muscular dystrophy of the present invention is expected to be a practical therapeutic drug for muscular dystrophy for which no effective therapeutic drug is present yet.

EXAMPLES

Hereinafter, the present invention will be described in more detail with reference to Examples, but the present invention is not restricted by the following Examples and can be suitably modified within the scope described above or below, and such modifications are also included in the technical scope of the present invention.

Production Example 1

Purification of Caldecrin from Rat Pancreas

Twenty five rats obtained from Saitama Experimental Animals Supply Co., Ltd. were killed by administering Nembutal to take out pancreases therefrom. The obtained pancreases were crushed by a homogenizer (Product name: Polytron manufactured by Central Scientific Commerce, Inc.), and dehydrated by adding acetone. Then, 0.1 M Tris-HCl (pH 8.0) containing 2% NaCl was added thereto, and the mixture was filtrated after being stirred well. Cold acetone at a ratio of 0.4 by volume was added into the filtrate to make acetone concentration 30% by volume, and the filtrate was stirred for 30 minutes under a condition chilled with ice followed by centrifugation to give a supernatant. Further, a cold acetone at a ratio of 0.6 by volume was added to make the acetone concentration 60% by volume, and the mixture was stirred for 30 minutes under a condition chilled with ice followed by precipitation by centrifugation to give 30 to 60% acetone fraction. The obtained 30 to 60% acetone fraction was dissolved in distilled water and was further dialyzed with distilled water to remove the acetone. Further, 45% ammonium sulfate was added thereto, and the mixture was stirred at 4° C. for 30 minutes followed by centrifugation. Ammonium sulfate was added to the obtained supernatant so that the concentration became 60%, and the mixture was stirred at 4° C. for 30 minutes followed by centrifugation to obtain 45 to 60% ammonium sulfate fraction. The 45 to 60% ammonium sulfate fraction was dissolved in distilled water followed by lyophilization, and was kept in a dark cold place until the time of use.

The 45 to 60% ammonium sulfate fraction was dissolved in 50 mM acetic acid buffer solution (pH 5.5), and was dialyzed with the buffer solution followed by purification of the solution by Q-Sepharose Fast Flow Column, Superdex 75HR Column and Mono Q HR Column to obtain a protein.

The obtained protein was analyzed by HPLC using a reversed-phase column and SDS-polyacrylamide gel electrophoresis, and was identified to be a single protein. Additionally, the amino acid sequence of the protein was analyzed by a gas-phase sequencer, and the protein was identified as caldecrin since the amino acid sequence of SEQ ID No.1 was present at N-terminal or the proximity of N-terminal.

The caldecrin was dissolved in phosphate buffer solution to be a solution at concentration of 1 mg/mL followed by filtration and sterilization using a filter having a pore size of 0.22 μm. The filtrate was injected into sterilized vials in an amount of 1 mL for each. The each filtrate in vial was subjected to vacuum lyophilization followed by being stopped airtight, and was kept in a dark cold place until the time of use.

Production Example 2

Production of Pancreas Extract (PX)

In accordance with a method described in Takaoka et al., Acta Medica Nagasakiensia, vol. 13, No. 1-2, pp. 28-35, (1969), pancreas extract containing a plurality of elastase mixtures as main components was prepared. More specifically, into 10 g of a commercially available pig acetone powder (manufactured by Sigma), cold water in an amount of 10 times by weight ratio was added, and the mixture was subjected to extraction for 1 hour in a cold place followed by filtration. Then diluted hydrochloric acid was added to the obtained filtrate for adjusting pH to 4 to form precipitate. The precipitate was separated by centrifugation at 3,000 rpm for 10 minutes. The precipitate was dissolved in water, and diluted hydrochloric acid was added to the solution to adjust pH to 5.4. The resultant precipitate was separated by centrifugation. Diluted hydrochloric acid was added to the obtained supernatant for readjusting pH to 4.0 to generate precipitate. Further, the precipitate was separated by centrifugation, and was dissolved in purified water. Into the solution, 40% ammonium sulfate was added, and the mixture was kept still at room temperature for 1 hour. The resultant precipitate was separated by centrifugation. Water was added to the obtained precipitate to be dissolved, and the mixture was subjected to dialysis using a dialysis tube (Cut off 3,500<) with purified water. Further, 80% ammonium sulfate was added to the dialysate to obtain precipitate. The precipitate was dissolved again in purified water followed by dialysis. The obtained purified solution was subjected to lyophilization to obtain 1.2 mg of pancreas extract. The extract was confirmed to be a protein by Biuret method. The obtained pancreas extract was sterilized in the same manner as in Production example 1.

Production Example 3

Production of Caldecrin Using a Gene

PCR reaction was carried out using human caldecrin cDNA (cloned from cDNA library of Stratagene) as a template and Bsa I primer (S: SEQ ID No.9, AS: SEQ ID No.10) as primers. More specifically, Pfu DNA polymerase available from Stratagene was used as polymerase, and a cycle of the reactions at 96° C. for 45 seconds, at 50° C. for 1 minute, and at 72° C. for 2 minutes was repeated 30 times. The amplified human caldecrin cDNA was subjected to ligation with Bsa I site of pEXPR-IBA 3 vector. The vector is one in which DNA sequence of STREP-tag is ligated to 3' target DNA in order to fuse a streptavidin binding tag (STREP-tagII) to C-terminal of a protein to be obtained finally. The vector was transfected with *Escherichia coli* (Top 10 manufactured by Invitrogen), and the *Escherichia coli* was cultured in LB/Amp medium at 37° C. over a night. Next, the vector DNA was purified using NucleoSpin Extract II kit manufactured by Macherey-Nagel to obtain human caldecrin cDNA in which Strep-tag was fused to the C-terminal.

Using the obtained cDNA as a template, and DNA of SEQ ID No.11 as the Sense primer and STREP-tag-NotI DNA of SEQ ID No.12 as the Antisense primer, polymerase chain reaction was carried out. More specifically, Pfu DNA polymerase available from Stratagene as polymerase was used, and a cycle of the reactions at 94° C. for 30 seconds, at 60° C. for 30 seconds, and at 68° C. for 2 minutes was repeated 32 times. The amplified human caldecrin DNA was subjected to ligation with Eco RV-Not I site of pIRES-bleo3 vector. The vector was transfected with *Escherichia coli* (DH5α manufactured by TAKARA) to purify DNA by the same conditions as the above. With a use of Lipofectin Reagent, the obtained DNA was transfected with HEK293T cell manufactured by Gibco BRL. Separately, bleomycin in an amount of 400 μg/mL was added to DMEM GlutaMAX-I medium manufactured by Gibco BRL (10% FBS, 100 μg/mL penicillin G, 0.25 μg/mL streptomycin). In the medium, the transfected HEK293T cells were selectively cultured at 37° C. for 14 days.

The medium was centrifuged at 700 rpm for 10 minutes, and 65% ammonium sulfate was added to the supernatant to precipitate protein. After centrifugation at 12,000 rpm for 30 minutes, the obtained precipitate was dissolved by addition of washing buffer solution (100 mM Tris-HCl pH 8, 150 mM NaCl, 1 mM EDTA). The solution was applied to Strept-Tactin immobilized gel (Strep-Tactin Superflow column) and washed with the buffer solution for cleaning, and then the protein was eluted by an elution buffer containing Destiobiotin, 100 mM Tris-HCl pH8, 150 mM NaCl and 1 mM EDTA containing. The obtained eluate was subjected to dialysis by 20 mM Tris-HCl (pH 7.0), followed by being applied to Mono S ion-exchange column equilibrated by 20 mM Tris-HCl (pH 7.0) and eluted by 20 mM Tris-HCl (pH 7.0) containing 500 mM NaCl to give pro-type human caldecrin which does not show protease activity. The pro-type human caldecrin was fused with a tag at C-terminal for binding to Strept-Tactin.

Production Example 4

Preparation of Human Caldecrin Gene Expression Vector

By the same conditions as Production example 3, PCR was carried out using phCaldecrin-IRES-bleo as a template and Sac I-ATG caldecrin and STREP-tag-Not I as primers to amplify human caldecrin DNA. The obtained DNA was incorporated into Sac I-Not I site of pIRES-hrGFP. The vector was encapsulated in liposome of Genome One-Neo available from ISHIHARA SANGYO KAISHA, LTD. Genome One-Neo is a vector containing of a membrane of hemagglutinating virus of Japan (HVJ). The vector, while retaining cell adhesion activity and completely inactivating virus proliferation activity thereof, is incorporated to a cell together with a gene for treatment by endocytosis. Therefore, the obtained cell incorporating human caldecrin gene expression vector can express human caldecrin gene and produce caldecrin.

Test Example 1

Eight-week old C57BL/6J (dy/dy) male mice obtained from Central Institute for Experimental Animals were divided into three groups each consisting of three mice. The mice were mutant-type muscular dystrophy-affected model mice, and were not able to move their lower limbs and feed themselves with food and water, showing an incidence of symptoms similar to muscular dystrophy. On a morning after fasting overnight after one week of habituation, caldecrin prepared in the same manner as Production example 1 at a dose of 100 μg per 1 kg of the body weight was administered to one side of femoral muscle of mice of two groups by intramuscular injection, while phosphate buffer solution was administered to a control group. After the administration, blood sample was taken at 3 hours and 6 hours respectively to measure concentration (mg/dl) of serum urea nitrogen (hereinafter abbreviated as "BUN" occasionally) using urea nitrogen B-Test Wako kit manufactured by Wako Pure Chemical Industries, Ltd. The results are shown in Table 1. The values in the table are mean±standard deviation, and "Proportion" shows the rate of BUN value of caldecrin administration group with respect to control group.

TABLE 1

|  |  | Control group | Caldecrin-administration group | Proportion (%) |
|---|---|---|---|---|
| BUN value (mg/dl) | 3 hours after | 28.92 ± 2.08 | 21.02 ± 1.16 | 72.7 |
|  | 6 hours after | 25.23 ± 1.13 | 20.47 ± 0.91 | 81.1 |

As the above results, urea nitrogen level in serum was clearly lowered to about 70 to 80% compared with the control group by the administration of caldecrin. Since urea nitrogen level in serum increases with a collapse of muscular tissues, it has been demonstrated that caldecrin can suppress the collapse of muscular tissues.

Test Example 2

Two kinds of dy mice, i.e. mutant-type (dy/dy) and wild-type, were divided into three groups with three mice each. Separately, human caldecrin obtained in Production example 3 was activated with trypsin in an amount of one fiftieth of the caldecrin for 30 minutes, and protease activity was suppressed with 1 mM of PMSF. After habituation for 1 week, the human caldecrin was administered to a group of mice by injection at a dose of 100 µg per 1 kg of the body weight for 4 consecutive days. To the control group, phosphate buffer solution was administered in the same manner. These groups fasted overnight before a last administration, and they were killed 3 hours after the last administration to collect blood sample on the following day.

To the remaining one group, a solution of 10 µg of DNA/100 µL prepared from human caldecrin gene expression vector of Production example 4 was administered by intramuscular injection to one side of femoral muscle at a dose of 100 µL per mouse. Since it takes at least one day from the administration of DNA to the expression of protein, mice were killed after five days from the administration. The mice fasted one day before being killed, and blood sample was taken after the mice were killed.

Figure 1:
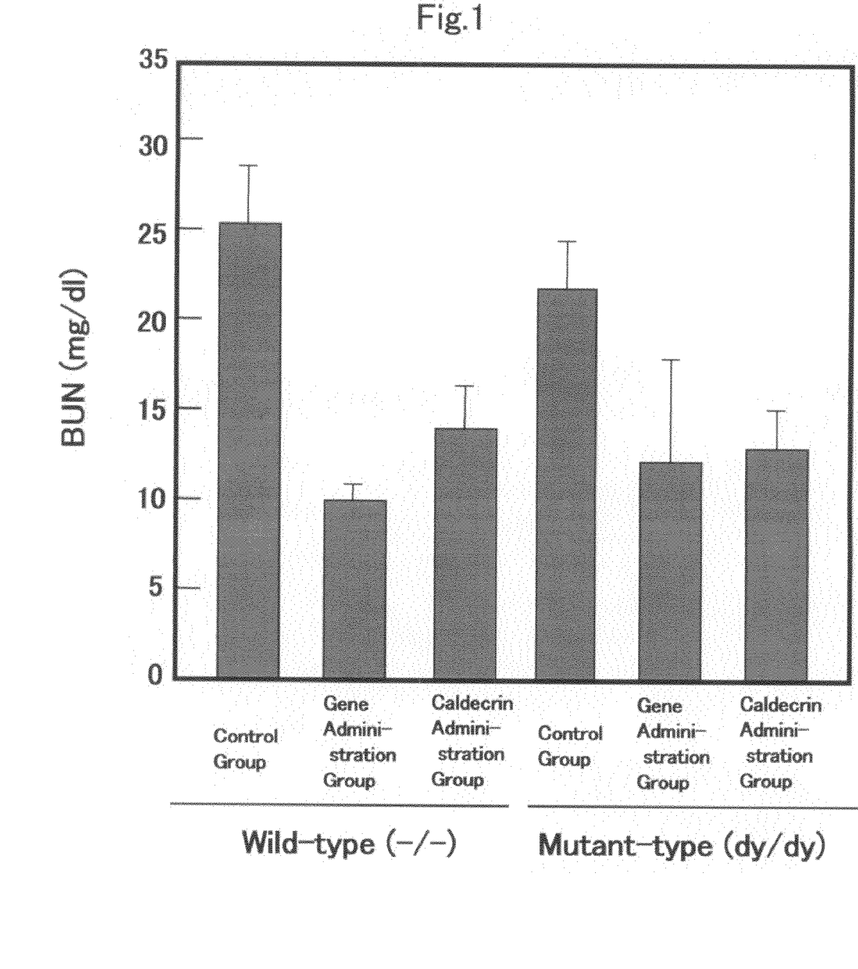
FIG. 1 is a diagram showing the change of serum urea nitrogen level when human caldecrin or human caldecrin gene expression vector is administered to a muscular dystrophy-affected model mouse.

Serum was separated from blood samples taken from each group to determine BUN concentration (mg/dl). The results are shown in FIG. 1. As shown in FIG. 1, in both mutant-type and wild-type dy mice, BUN level in serum could be lowered by administration of caldecrin.

Test Example 3

In the same manner as Test example 2, after mutant-type dy/dy mice were habituated for 1 week while normal mice of a same kind were used as a control group, human caldecrin of Production example 3 and human caldecrin gene transfection liposome of Production example 4 were administered. The human caldecrin was administered by intraperitoneal injection at a dose of 100 µg per 1 kg of the body weight for 4 consecutive days, and the mice were killed 3 hours after the last administration. The human caldecrin gene transfection liposome was injected to one side of femoral muscle at a dose of 100 µL (including 10 µg of DNA) in a state of solution per one mouse and the mice were killed after 5 days. To the control group, phosphate buffer solution was administered by the same conditions as the administration of human caldecrin. Each group fasted a day before being killed.

To each group, 1% Evans blue (EV) dissolved in PBS was administered by injection 24 hours before the mice were killed at a dose of 50 µL per 10 g of the body weight. The Evans blue does not penetrate into an undamaged cell, but when a cell membrane is damaged, the Evans blue penetrates into the cell. After mice were killed, femoral muscle was taken out and a part of it was fixed with 10% formalin while another part thereof was frozen. In the group administered human caldecrin gene transfection liposome, the femoral muscle was taken out from an opposite side of the leg which was subjected to intramuscular injection.

Figure 2:
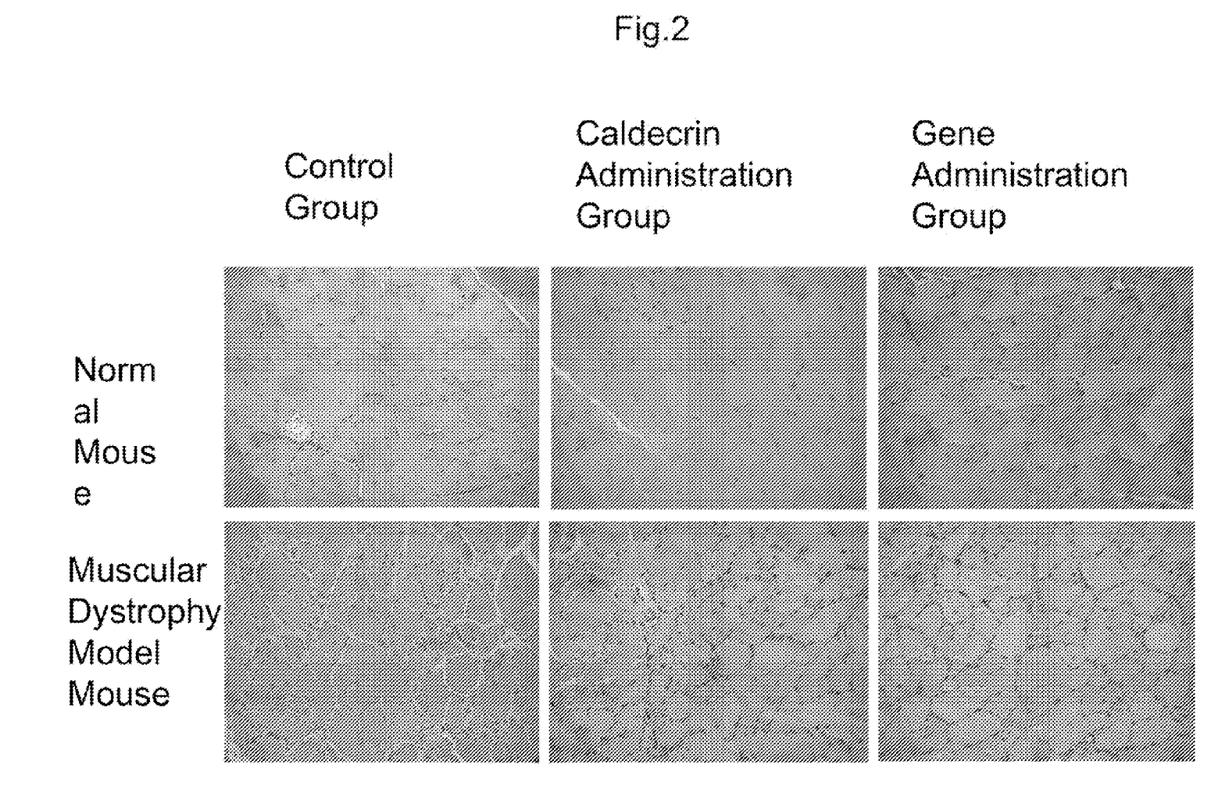
FIG. 2 is photographs showing results of H. E. stain of muscular tissue in a normal mouse and a muscular dystrophy-affected model mouse to which human caldecrin or human caldecrin gene expression vector was administered.

From formalin-fixed muscle, a slice of the femoral muscle at a maximum cross-section was obtained to be subjected to HE stain. Results are shown in FIG. 2. As in FIG. 2, muscular tissue of a normal mouse had less irregularity of cross-section of muscle fiber, and a dark-colored nucleus was found around the muscle fiber. However, in muscular tissue of the control group of the muscular dystrophy-affected model mouse, due to modification and necrosis of muscle fiber, muscle fibers which were thinner, in other words, having smaller area of cross-section were formed, and nucleuses were transferred around a center of the muscle fiber. On the other hand, in a mouse administered caldecrin and a caldecrin gene, a basic structure of the muscular tissue was well maintained, and symptoms were clearly improved.

Figure 3:
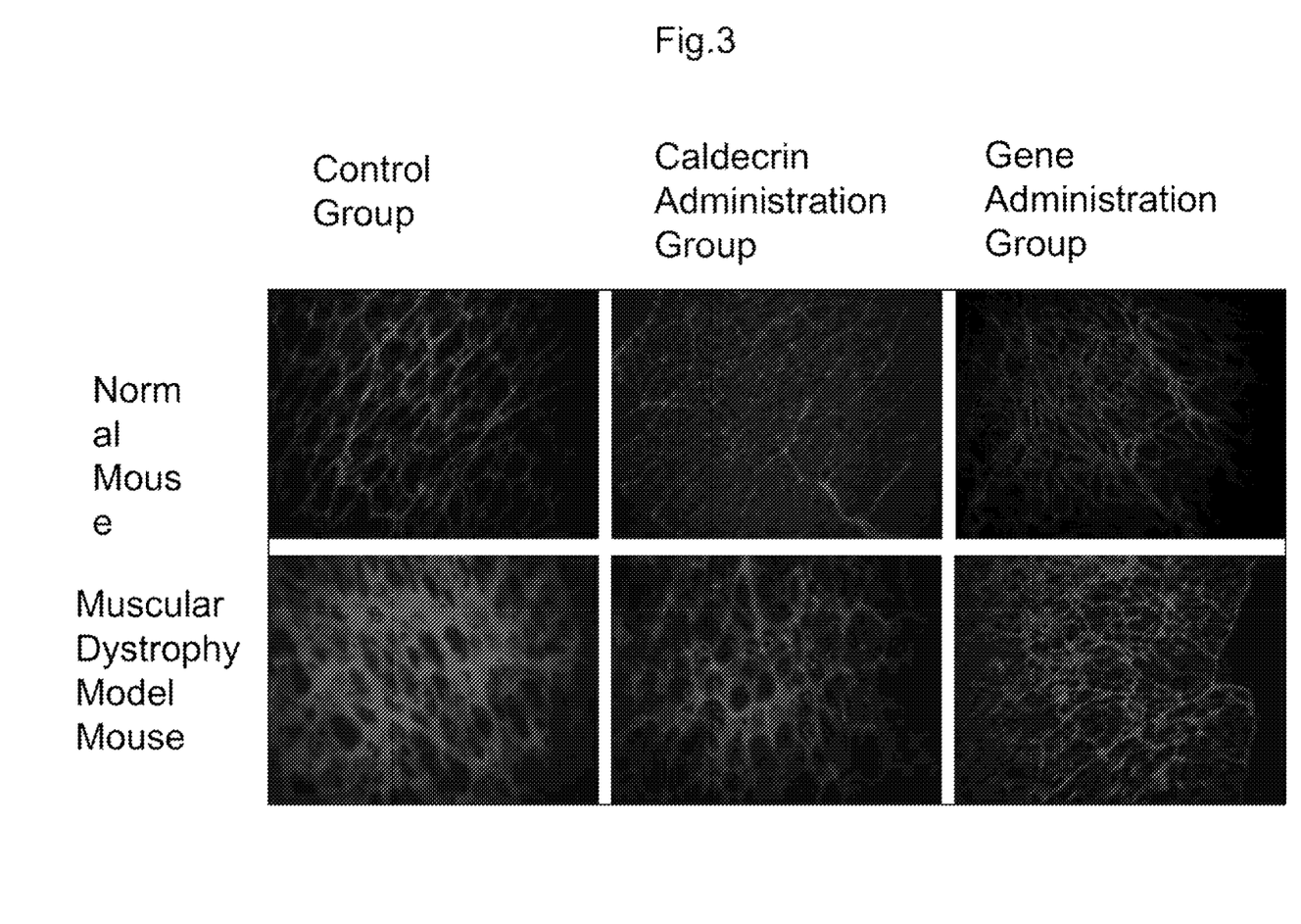
FIG. 3 is fluorescent microscope photographs by autonomous fluorescence of Evans blue showing conditions of muscular tissues in a normal mouse and a muscular dystrophy-affected model mouse to which human caldecrin or human caldecrin gene expression vector was administered.

From frozen femoral muscle, a frozen section of 10 µm was prepared and autonomous fluorescence by Evans blue was observed using fluorescent microscope. Photographs of the fluorescent microscope are shown in FIG. 3. As shown in FIG. 3, when the images of the tissue were observed using fluorescent microscope, red fluorescent caused by Evans blue administered one day before killing was localized around the muscle fiber because muscular tissue was well maintained in a normal mouse. Evans blue was specifically incorporated into collapsed muscle fiber to stain the fiber. Therefore, the results show that there was no damage in normal mouse since almost no Evans blue was present in muscular cell. The same can be said for mice administered caldecrin or transfected with caldecrin gene. On the other hand, in muscular tissue of muscular dystrophy-affected model mouse, an irregularity of area of cross-section of muscle fiber due to modification and necrosis of muscle fiber was observed, and Evans blue penetrated into the muscle fiber. In contrast, in muscular tissue administered caldecrin or a caldecrin gene, the ratio of red fluorescent image was clearly decreased though intrusion of Evans blue into a part of muscle fiber was observed, demonstrating an effect of caldecrin and caldecrin gene on suppressing collapse of muscular tissue.

Test Example 4

Six-week old BALB/cCr Slc male mice fasted from one day before the test. Separately, the human caldecrin obtained in Production example 3 or the pig pancreas extract obtained in Production example 2 was dissolved in phosphate buffer solution to prepare a solution of a concentration of 0.01 mg/mL. The mice were divided into groups having 4 or 5 mice each, and were intraperitoneally-injected with a phosphate buffer solution alone, a human caldecrin solution, or a pancreas extract solution at a dose of 0.1 mL per 10 g of the body weight. Five hours after the administration, blood sample was taken from the heart, and serum urea nitrogen level (mg/dl) and creatinine level (mg/dl) were determined using BUN Test Wako and creatinine Test Wako kit. The result of the serum urea nitrogen level is shown in Table 2 while the result of creatinine level is shown in Table 3.

TABLE 2

| | Number of mice | BUN (mg/dl) ± standard deviation | t-TEST | Proportion (%) |
|---|---|---|---|---|
| Control group | 4 | 26.6 ± 3.00 | | 100 |
| Caldecrin-administration Group | 5 | 22.3 ± 1.64 | 0.0142 | 83.8 |
| PX-administration group | 4 | 25.4 ± 4.08 | 0.318 | 95.5 |

TABLE 3

| | Creatinine (mg/dl) ± standard deviation | t-TEST | Proportion (%) | BUN/creatinine |
|---|---|---|---|---|
| Control group | 1.44 ± 0.00297 | | 100 | 18.5 |
| Caldecrin-administration Group | 1.53 ± 0.1 | 0.123 | 106.3 | 14.6 |
| PX-administration group | 1.95 ± 0.0016 | $9.63 \times 10^{-5}$ | 135 | 13.0 |

As in the above results, although serum urea nitrogen level could be lowered by an administration of pancreas extract, the level was further lowered compared with the case of the administration of caldecrin. Therefore, it has been demonstrated that caldecrin can suppress the collapse of muscular tissue caused by muscular dystrophy more effectively.

Further, creatinine level in blood was rather increased by pancreas extract. The creatinine is basically supposed to be discharged into urine via kidney, so that the creatinine level in blood is used for evaluating renal function. Therefore, the results strongly suggest that the renal function was damaged by administration of pancreas extract.

On the other hand, when caldecrin was administered, an increase in the creatinine level in blood was markedly suppressed, and the level was almost the same as the control group. This fact suggests that muscular dystrophy can be treated by the administration of caldecrin without affecting adversely on renal function.

As described above, although caldecrin is a protein derived from pancreas and having a DNA sequence similar to elastase, caldecrin has much higher decreasing-effect on serum urea nitrogen than PX which is a crude extract of pancreas including elastase mixture as a main component. While PX has a possibility of affecting adversely on renal function since PX increases creatinine level in blood, caldecrin does not have such a defect. Therefore, caldecrin and a gene thereof are extremely effective as agents for treating muscular dystrophy for which no effective therapeutic agent exists.

What is claimed is:

1. A method for treating muscular dystrophy, comprising the step of administering to a subject in need thereof a composition comprising a therapeutically effective amount of a caldecrin protein.

2. A method for treating muscular dystrophy, comprising the step of administering to a subject in need thereof a composition comprising a therapeutically effective amount of a caldecrin protein selected from (a) to (d):
   (a) a protein having the amino acid sequence of SEQ ID NO:1;
   (b) a protein having the amino acid sequence of SEQ ID NO:2;
   (c) a protein formed by deletion, substitution and/or addition of 1 to 10 amino acids of a protein having the amino acid sequence of SEQ ID NO:1, and having a therapeutic effect on muscular dystrophy; and
   (d) a protein formed by deletion, substitution and/or addition of 1 to 10 amino acids of a protein having the amino acid sequence of SEQ ID NO:2, and having a therapeutic effect on muscular dystrophy.

3. The method according to claim 2, wherein the protein (b) is administered.

4. The method according to claim 2, wherein the protein (d) is administered.

5. The method according to claim 2, wherein the number of deleted, substituted and/or added amino acids is 1 to 5.

6. The method according to claim 2, wherein the number of deleted, substituted and/or added amino acids is 1 or 2.

* * * * *